United States Patent [19]
Whistler

[11] Patent Number: 5,486,507
[45] Date of Patent: Jan. 23, 1996

[54] POROUS PARTICLE AGGREGATE AND METHOD THEREFOR

[75] Inventor: Roy L. Whistler, West Lafayette, Ind.

[73] Assignee: Fuisz Technologies Ltd., Chantilly, Va.

[21] Appl. No.: 182,442

[22] Filed: Jan. 14, 1994

[51] Int. Cl.⁶ ............... A61K 31/715; C07H 1/00; C08B 30/00; C08B 31/00
[52] U.S. Cl. ............... 514/54; 514/60; 530/350; 536/56; 536/114; 536/102; 536/103; 536/123.1
[58] Field of Search ................... 536/102, 103, 536/56, 114, 123.1; 514/54, 60; 530/350

[56] References Cited

U.S. PATENT DOCUMENTS

| | | | |
|---|---|---|---|
| 4,144,079 | 3/1979 | Smith | 524/36 |
| 4,159,982 | 7/1979 | Hermansson | 530/360 |
| 4,549,909 | 10/1985 | Samuel et al. | 127/33 |
| 4,612,284 | 9/1986 | Pickens et al. | 435/96 |
| 4,985,082 | 1/1991 | Whistler | 536/102 |
| 5,051,133 | 9/1991 | Nagai et al. | 536/102 |
| 5,346,892 | 9/1994 | Fitt et al. | 536/102 |

*Primary Examiner*—Michael G. Wityshyn
*Assistant Examiner*—Everett White
*Attorney, Agent, or Firm*—Hoffmann & Baron

[57] ABSTRACT

A porous aggregate having a high intraaggregate reticular volume for releasable containment of functional substances is described. The porous aggregates comprise discrete particles, preferably starch granules, bound together at least at their points of contact in the aggregates. The surfaces of the discrete particles cooperate to define an intraaggregate reticulate volume. The porous aggregate composition of this invention finds use as a high capacity carrier of functional substances for a wide variety of applications, in which the functional substance is released from the aggregate composition under the influence of mechanical compression/disintegration, by degradation or dissolution of the binder and/or particulate components, or by diffusion from the porous surface.

13 Claims, No Drawings

POROUS PARTICLE AGGREGATE AND METHOD THEREFOR

BACKGROUND AND SUMMARY OF THE INVENTION

This invention relates to particulate carriers for functional substances. More particularly, this invention is directed to particle aggregates having high porosity and a large intraaggregate reticulate volume for containment of functional substances. The present aggregate compositions are economically manufactured to have predetermined release characteristics and other desired physical properties.

There has been a significant research and development effort directed to the definition and manufacture of carriers for functional substances for a wide variety of commercial applications. Ideal carrier compositions are those that inherently exhibit high capacity for carrying/containment of functional substances, those which work to enhance or prolong the functionality of the contained or carried substance, and those which can be economically manufactured to meet the unique specifications required for each targeted application. Such are the characteristics of the composition of the present invention.

In accordance with this invention, there is provided a versatile, low cost porous composition having a high void volume and thus a high capacity for containment for functional substances. The composition comprises free flowing aggregates of discrete particles, most preferably starch granules, bound together with a binder at their points of contact in the aggregate. The use of starch granules as the particle component of the present carrier composition provides surprisingly uniform spherical aggregates ranging in diameter from about 15 to about 150 microns, depending on the size distribution of the component starch granules. The surfaces of the aggregated particles cooperate to define an intraaggregate reticular volume for releasable containment of the functional substances. Advantageously the physical/chemical characteristics of the composition can be readily adjusted to meet the functional requirement of each targeted application by selection of the particle and binder components.

The particle aggregate compositions in accordance with this invention are prepared by forming a suspension of the particulate component in a solution of a binder and spray-drying the resulting suspension utilizing art-recognized spray drying equipment/technology. The particulate components can be pre-treated to promote their compatibility with the targeted functional substance and to impart other properties such as hardness and solubility characteristics appropriate for the contemplated carrier application. Further, the binder, typically a polymeric material exhibiting affinity for the particle component, can be selected according to its chemical and physical characteristics to optimize functionality of the particulate aggregates as a carrier in a targeted application. Thus the binder component can be selected with view of its solubility, its chemical reactivity, for example, its bioerodability or biodegradability, as appropriate to optimize functionality of the particle aggregates of the invention. Finally, the present aggregate compositions can be coated to provide additional functionality.

Functional substances can be easily introduced into the reticular volume of the present porous aggregates. The high intraaggregate reticular volume and high internal surface area of the present aggregate compositions allow high loading of functional substances. The loaded porous aggregate compositions of this invention are free flowing powders which facilitate handling and mixing of the functional substance in product formulations and further provides a matrix for sustained or prolonged release of the carried functional substance. Additionally, it is contemplated that the particle aggregates in accordance with this invention will exhibit functionality independent of their use as a carrier for functional substances. Thus, they may be used in prepared foods that require minute gritty character, either in mouth feel or in appearance. The particle aggregate composition in accordance with this invention has utility in the areas of food/nutrition, the preparation of topical creams and lotions, deodorant/antiperspirants, cosmetics, agricultural products, and products for human and veterinary medicine. The present compositions can be designed to enhance and prolong the functional characteristics of contained functional compositions. Alternatively, the present composition can function to protect the contained functional substance from premature degradation. For example, orally administered pharmaceutical compositions can be formulated with/in the aggregate compositions, preferably the granular starch-based compositions of this invention, to provide an enteric formulation which functions to protect the active substance from the acid/digestive conditions of the stomach and thereafter release the active substance in the small intestine.

DETAILED DESCRIPTION OF THE INVENTION

In accordance with the present invention, there is provided a porous aggregate of discrete particles. The particle components of the present aggregates typically have an average particle size of about 1 to about 100 microns in their largest dimension. The particles are bound together with a binder, at least at their points of contact in the aggregate, so that the surfaces of the aggregated particles cooperate to define an intraaggregate reticular volume into which one can introduce functional substances. The contained substances are capable of being released from the aggregate over a period of time commensurate with the diffusion of the contained functional substance into the surrounding environment with or without the cooperation of disintegration of the aggregate due to solubilization or bioerosion/biodegradation of the binder or particulate components of the aggregate.

The present particle aggregate composition is prepared quite simply and economically by suspending the particles in a solution of a suitable binder and thereafter spray-drying the particulate suspension using art-recognized spray-drying methodology/equipment. Optionally the particle aggregate can be further processed by applying a polymer coating to the surface of the particulate aggregate after it is formed, either before or after a functional substance is introduced into the intraaggregate reticular volume. The coating process can be carried out using spray coater equipment such as that used in tablet manufacture or in art-recognized fluidized bed-type coating equipment.

The discrete particles utilized in preparing the present porous aggregates are preferably selected to have an average particle size of about 1 to about 100 microns, more preferably about 1 to about 75 microns, in their largest dimension. Exemplary of such particulate material useful in accordance with this invention are starch granules, particulate cellulosic materials such as micronized wood pulp or grain hulls, and particulate polymer materials such as those sold in the art as flattening agents for coating compositions, for example, Pergopak® polymer particles sold by Martinswerk. Preferred particulate materials for use in accordance with this invention are granular starches, including native granular starches from various vegetable sources such as corn, barley, rice and wheat, which are known for their somewhat larger starch granules, and as well, from vegetable sources known to produce small starch granules such as amaranth, quinoa, dasheen, cow cockle, pigweed and Chinese taro. Small starch granules such as those from amaranth and the size classified small starch fraction of wheat starch are particularly preferred for use in accordance with this invention.

Granular starches, presumably due to their inherent spherical or spheroidal structure, form substantially spherical granular starch aggregates when used as the particulate component of the aggregate compositions of the present invention. Optionally the granular starch component of the preferred embodiments of present composition can comprise chemically modified granular starches including granular starches that have been rendered microporous by being subjected to partial hydrolysis with acid or enzyme. Further, granular firmness and surface characteristics can be advantageously adjusted by pretreatment of the granules intended for use in the present particle aggregate compositions. Thus, for example, a greater degree of structural integrity and firmness can be introduced by pre-treating granular starch with an effective amount of a bifunctional starch-reactive chemical cross-linking agent. Any of a wide variety of art-recognized starch cross-linking agents, including those recognized as food-acceptable by the Food and Drug Administration, can be used. Suitable cross-linking agents include phosphates such as sodium trimetaphosphate, dicarboxylic acid derivatives, particularly $C_2$–$C_6$ dicarboxylic acids, including maleic and glutaric acid, phosphorous oxychloride, epichlorohydrin, and $\beta,\beta$-dichlorodiethylether. Granular starches are rendered more resistant to mechanical damage, to swelling and to dissolution with increased degree of cross-linking.

Further the surface characteristics of the granular starches for use in preparation of the particle aggregates of the present invention, and thus the surface characteristics and absorptive capacity of the resultant aggregates, can be affected by other surface modification of the granular starch component. Thus granular starches intended for use in accordance with the present invention can be pre-treated with surface-modifying agents to enhance granule compatibility with functional substances targeted for use with the porous particle aggregate. If the substance to be introduced into the reticular volume of the particle aggregate composition has a predominant lipid character, the starch granules can be treated to render their surfaces more lipophilic. Thus, the granules can be surface treated with solutions of amphophilic polymers, or the surfaces of the granules can be chemically derivatized, for example, by reacting the granules with stearyl- or octyl-succinic acid anhydride. The granule surfaces are thereby rendered more lipophilic and more compatible with functional substances having a predominant lipid character. Surface characteristics of the granular starch component of the present compositions can also be modified for enhanced lipophilicity by pre-treatment with esterifying agents such as long chain fatty acids or derivatives thereof, or by etherification with long chain fatty halides. Treatment with acetic anhydride will also provide some lipophilic character to the granules, but a higher level of derivatization is required.

The porous particulate aggregates in accordance with this invention are prepared by spray-drying a slurry of particles in a solution of a binder component. The chemical nature of the binder is not critical, except to the extent the binder should exhibit some threshold affinity for the surface of the discrete particles so that it can operate to bind the aggregated particulates together at least at their points of contact during the spray-drying process. Inherently, too, the binder component must have some threshold solubility in the liquid used to suspend the particle component prior to the spray drying operation. That liquid is typically water, however, other liquids such as $C_1$–$C_6$ alcohols, ethers and ketones may also be employed where the targeted functionality of the porous particle aggregate requires use of a binder not having the threshold solubility in water. Preferably, however, the porous particle aggregates in accordance with this invention are prepared by spray-drying aqueous suspensions of discrete particles, preferably starch granules, suspended in an aqueous solution of a binder.

There exists a wide variety of suitable binders that can be used in the formation of the present particle aggregates. They are, most typically, polymer compositions exhibiting the requisite degree of solubility in the liquid carrier for the particle suspension spray dried to form the porous aggregates. The polymer materials can be water soluble, water insoluble, biodegradable/bioerodable, not biodegradable, natural, synthetic, or semisynthetic—the binder to be selected for any particular application being dependent on the desired functionality, chemical/physical stability and release characteristics of the targeted aggregate in accordance with this invention. Preferred binders for use in accordance with this invention are biodegradable polymers such as polysaccharides including gums such as guar and locust bean gums, pectins, agar, alginate, gelatin, dextrins, dextran and derivatized starches and cellulosic materials such as carboxymethyl cellulose, hydroxymethyl cellulose, hydroxypropyl cellulose, and the like, proteins, particularly proteins other than those endogenous to the starch granules used to form the aggregates, and polyesters. Polysaccharides are preferred binders for use in accordance with the present invention. The binder components can also be non-biodegradable, synthetic or semi-synthetic polymers, such as polyvinyl alcohol, poly-N-vinyl-2-pyrrolidone, and polymers or co-polymers of acrylic or methacrylic acid and amide derivatives thereof, including polyacrylamide.

In accordance with the method embodiment of the present invention, porous aggregates of discrete particles are prepared by spray-drying a suspension of such particles in a solution of a suitable binder utilizing conventional spray-drying equipment/conditions. One limitation on the spray-drying process is the stability of the particle component. Specifically, when spray-drying granular starch suspensions in aqueous binder solutions, it is very much preferred that the temperature in the spray-drying operation is not so high as to effect gelatinization of the starch granules.

The binder component is typically functional at very low levels, most preferably about 0.1 to about 2% by weight of the solution/suspension. The particulate component usually constitutes between about 2 and about 20 weight percent of the suspension prepared for spray-drying in accordance with this invention to produce the present porous particle aggregates.

The porous particle aggregate composition in accordance with this invention exhibits physical and chemical characteristics dependent on the constituent discrete particles and the binder component. The aggregates range in size from about 10 microns to about 250 microns, more typically between about 15 and about 150 microns, most typically between about 10 and about 50 microns. The size and shape of the present particle aggregates depend significantly on the shape and particle size distribution of the component discrete particles. Thus when the preferred particle component, starch granules, are utilized to form the present porous aggregates, the aggregates assume a remarkably uniform spherical shape with the individual granules being bound together with the binder components at their points of contact. The surfaces of the aggregated starch granules cooperate to define an intraaggregate reticular volume for releasable containment of a functional substance.

The size, shape and particle size distribution of the porous particulate aggregates prepared in accordance with this invention are also dependent on the conditions selected for the spray-drying operation. Conventional spray-drying parameters, however, used to form the preferred starch-granule-based aggregates in accordance with this invention, produce surprisingly uniform porous, spherical aggregates.

The porous particle aggregate composition of the present invention is advantageously utilized as a carrier for a wide range of functional substances. The term "functional substances" as used herein to describe the present invention refers to any compound or composition which inherently possesses biological or other functional activity and which exhibits such activity to achieve some useful result when applied or used in a manner adapted to take advantage of such activity. Exemplary of such substances which can be absorbed into the intraaggregate reticular volume of such aggregates in accordance with such invention are salad oils, flavors, insect repellants, insecticides, herbicides, perfumes, moisturizers, soaps, antiperspirants, waxes, body creams and lotions, fertilizers, minerals, vitamins, bacteriostats, and therapeutic drug substances. Such functional substances can be absorbed or otherwise introduced into the porous aggregates of the present invention either by spraying solutions of such substances onto the prepared aggregates, adding such substances to the particle slurries prior to the spray drying process, or by adding the aggregates to solutions of said substances wherein the solvent for such substances is selected so as not to prematurely dissolve or otherwise disrupt the aggregate binder component. The product aggregates containing functional substances within the reticular volume defined by the surfaces of the aggregated particles can be isolated in the process utilizing art-recognized techniques such as filtration, centrification, air classification and drying. The degree of loading of functional substances into the porous aggregates can be controlled in part by adjusting the concentration of the functional substance in the solutions used to load the aggregate matrices. Higher concentrations of the loaded material can be achieved using more concentrated solutions of the substances and by repeating the loading procedure. Preferably the substances are introduced into the porous particulate aggregates either as a component of the spray dried slurry or suspension used to form the aggregates, or as in solution in an inert, relatively low boiling solvent, which can be removed by evaporation following loading of the aggregate matrix. A hydrophobic liquid, such as a flavor oil, can be loaded into the aggregate by simply allowing the oil to soak into the porous aggregate.

The release characteristics and other physical properties of the particulate aggregates in accordance with this invention can be further modified by coating the aggregates following their preparation with a solution of the same or a different binder/polymer. The coating operation is preferably carried out after the loading of the aggregates with the desired functional substance. The coating operation can be accomplished simply by spraying the porous particulate aggregate composition with a dilute solution of a polymer which may be the same or different from that used as the binder component of the aggregate composition. The coating operation can be conducted in spray coater type equipment such as that used for conventional tablet coating operations or in conventional fluidized bed-type coating equipment. The polymer utilized in the optional aggregate coating operation can be selected to optimize the targeted functionality of the aggregate carrier composition. Suitable polymers include any of those mentioned above as binder components and as well other art-recognized coating compositions utilized in conventional tablet coating applications.

The porous particle aggregates in accordance with this invention can be used, without added functional substances, as a bulking agent or to impart other desirable organoleptic characteristics such as mouth feel, in various prepared foods. Preferably, however, the present compositions are used as carrier and excipient for functional substances to enhance or prolong substance functionality. Thus, for example, the present composition can be utilized as a carrier for functional liquids, essentially converting them in form to free-flowing powders which can be used as a substitute for such functional substances in compositions to promote and/or prolong substance functionality. The carried or contained functional substances are released from the porous particulate aggregate, by simple diffusion, or upon mechanical compression or by chemical degradation or simple dissolution of the binder and/or particle components. Thus, for example, it has been found that granular starch aggregates in accordance with this invention utilizing a guar gum or carboxymethyl cellulose binder can be "loaded" with a flavor oil and used as a component of chewing gum to prolong flavor release.

The following Examples are presented to illustrate the present invention and should not in any way be construed as a limitation thereof.

EXAMPLE 1

Amaranth starch granules are slurried in a solution of about 0.5 to about 1% by weight of a commercial high viscosity guar gum to produce strong spherical aggregates. The spherical aggregates range from about 10 to about 30 microns in diameter.

EXAMPLE 2

Granular amaranth starch was suspended in a 0.1% guar gum solution and spray dried to produce spherical aggregates having a size range of about 10 to about 30 microns. The aggregates were dispersed in mint oil, centrifuged and thereafter washed with ethanol in a fritted glass funnel and dried to provide a mint oil loaded aggregate composition containing about 35% by weight mint oil. The mint oil loaded starch aggregate composition was then spray coated with a 0.5% solution of guar gum. The coated spheres were essentially without odor, but released mint oil and odor when they were rubbed on a glass plate with a metal spatula.

EXAMPLE 3

A slurry of rice starch in a 1% aqueous solution of locust bean gum is spray dried to produce porous spherical aggregates having a high intraaggregate reticular volume.

EXAMPLE 4

The small granular fraction of wheat starch obtained by size classification of native wheat starch is slurried in an aqueous medium containing medium viscosity methylhydroxypropyl cellulose and spray dried to produce substantially spherical aggregates of small wheat starch granules.

The aggregates are dispersed in mint oil, centrifuged and thereafter washed with ethanol in a fritted glass funnel and dried to provide a mint oil loaded aggregate composition containing about 48% by weight mint oil. The mint oil loaded starch aggregate composition was then spray coated with a 0.5% solution of gelatin. The coated spheres were essentially without odor, but released mint oil and odor when they were rubbed on a glass plate with a metal spatula.

EXAMPLE 5

A suspension of 10 grams of a micronized wood pulp having an average particle size of about 5 to about 15 microns in 150 ml of ethanol containing 1.5% by weight of poly-N-vinyl-pyrrolidone is spray-dried in a conventional spray dryer to produce porous aggregates. The aggregate composition is dispersed in an aqueous solution of a pesticide, filtered and dried to provide a pesticide loaded particle aggregate composition in accordance with this invention.

EXAMPLE 6

Rice starch is slurried in 0.1% guar gum solution and spray dried to produce a free-flowing powder comprising spherical aggregates about 30 microns in diameter. The aggregates were non-hygroscopic and held their spherical shape under normal processing. The disintegration of the rice starch aggregates in water occurs over a period of time during which the intergranular binding gum is dissolved to allow disintegration of the spheres.

EXAMPLE 7

Commercial corn starch is dispersed into a 0.1% by weight solution of carboxymethyl cellulose and spray dried to yield aggregates of granular corn starch in accordance with this invention.

EXAMPLE 8

Rice starch is suspended for 5 minutes in a 0.2% solution of 20 DE (dextrose equivalent) starch dextrin and spray-dried at 120° C., spray nozzle setting to produce well defined spherical aggregates of rice starch.

EXAMPLE 9

Amaranth starch granules were suspended in a 0.1% sodium alginate solution and spray dried to form an alginate-bonded granular aggregate. The product is sprayed or briefly washed with a 1% calcium chloride solution to convert the sodium alginate binder to water insoluble calcium alginate. The resulting spheres exhibited enhanced stability under aqueous conditions up to temperatures near the gelatinization temperature of the starch component. The spheres are spray coated with a 1% sodium alginate solution and thereafter sprayed with calcium chloride solution to increase physical stability and water resistance. Mint oil filled/calcium alginate coated spheres are stabilized to oil leakage from the aggregate composition.

EXAMPLE 10

Aggregates of amaranth and wheat starch formed with either a carboxymethyl cellulose or locust bean gum binder are incorporated at 2% by weight into an ice cream composition prepared with but 50% of the normal fat content, without compromise of taste and mouth feel.

EXAMPLE 11

The small granular fraction of wheat starch is slurried in an aqueous solution of 0.1% gelatin and spray dried to produce porous, substantially spherical aggregates. The aggregate composition is slurried in an alcoholic solution of an orally effective antibiotic filtered and dried. The dried aggregates are coated in a fluidized bed coating machine with a 0.5% solution of ethyl cellulose of the type used for tablet coating. The coated aggregates are filled into capsules for oral administration.

I claim:

1. A composition comprising substantially spherical porous aggregates of starch granules bound together with a binder at least at their points of contact in said aggregates, the surfaces of the aggregated starch granules cooperating to define an intraaggregate reticulate volume for releasable containment of a functional substance, said aggregates having an average diameter of about 5 to about 250 microns.

2. The composition of claim 1 wherein the binder comprises a water soluble polymer not endogenous to the starch granules.

3. The composition of claim 1 further comprising a polymer coating applied to the surface of the aggregates.

4. The composition of claim 1 wherein the starch granules comprise partially hydrolyzed microporous starch granules.

5. The composition of claim 1 wherein the binder is a biodegradable or bioerodable polymer selected from the group consisting of polysaccharides, proteins, and polyesters not endogenous to the starch granules.

6. The composition of claim 1 further comprising a functional substance in the reticular volume of the porous aggregates.

7. The composition of claim 6 further comprising a polymer coating applied to the surfaces of the aggregates.

8. A composition comprising an aggregate of discrete starch particles, said starch particles having an average particle size of about 1 to about 100 microns in their largest dimension, said starch particles bound together with a binder not endogenous to the starch particles at least at their points of contact in said aggregate, the surfaces of said aggregated starch particles cooperating to define an intraaggregate reticulate volume adapted for releasable containment of functional substances.

9. The composition of claim 8 further comprising a functional substance in said reticulate volume.

10. The composition of claim 9 further comprising a polymer coating applied to the surface of the aggregate.

11. The composition of claim 10 wherein the polymer is selected from the group consisting of a polysaccharide, a polyvinyl alcohol, a poly-N-vinyl-pyrrolidone, a polyacrylamide, and an acrylic polymer or copolymer.

12. The composition of claim 8 wherein the binder is a biodegradable polymer.

13. The composition of claim 12 wherein the polymer is selected from the group consisting of polysaccharides, proteins, and polyesters.

* * * * *